United States Patent [19]
Smith et al.

[11] 4,066,750
[45] Jan. 3, 1978

[54] LACTOSYL SUBSTITUTED UREIDES IN RUMINANT FEEDSTUFF

[75] Inventors: Roy Henry Smith; Alexander Baxter McAllan, both of Reading, England

[73] Assignee: Astra Chemical Products AB, Sodertalje, Sweden

[21] Appl. No.: 710,637

[22] Filed: Aug. 2, 1976

[51] Int. Cl.² .......................... A61K 31/70; C07H 5/06
[52] U.S. Cl. ...................................... 424/180; 536/18; 536/22; 536/53
[58] Field of Search .................... 424/180; 536/18, 22, 536/4

[56] References Cited
U.S. PATENT DOCUMENTS

| | | | |
|---|---|---|---|
| 2,612,497 | 9/1952 | Meijer | 536/22 |
| 3,020,273 | 2/1962 | Steadman et al. | 536/22 |
| 3,149,033 | 9/1964 | Clark | 536/22 |
| 3,677,767 | 7/1972 | McNell | 424/180 |
| 3,843,799 | 10/1974 | Elofson | 424/180 |

Primary Examiner—Johnnie R. Brown
Attorney, Agent, or Firm—Brumbaugh, Graves, Donohue & Raymond

[57] ABSTRACT

The use of an ureide of the general formula

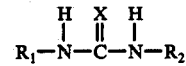

wherein $R_1$ is lactosyl, X is selected from the group consisting of O, S or =NH, and $R_2$ is selected from the group consisting of hydrogen, glucosyl and alkyl, as a non-protein nitrogen source in ruminant feedstuffs or feed supplements, and a process for preparing such an ureide.

6 Claims, No Drawings

LACTOSYL SUBSTITUTED UREIDES IN RUMINANT FEEDSTUFF

This invention relates to the use of a certain ureide derivatives as ruminant feedstuffs and feedstuff supplements containing sources of non-protein nitrogen (NPN), and to processes for the production of such ureide derivatives.

The object of the present invention is to obtain a possibility to feed ruminants with non-protein nitrogen in the form of urea, and thereby to avoid the formation of high concentrations of ammonia in rumen and in the blood, while simultaneously obtaining an additional source of energy.

A further object is to obtain a process for preparing ureide derivatives from cheap sources.

Urea is widely used as a source of non-protein nitrogen in the feeding of ruminants but its use suffers from the significant disadvantage that ammonia is often produced in the rumen by microbial breakdown more rapidly than it can be utilized by the rumen microorganisms and may attain levels which are toxic to the animal. In attempts to overcome this, NPN has been presented in forms in which the rate of ammonia production is decreased, e.g. as biuret, or urea has been given together with a urease inhibitor. These procedures reduce the risk of toxicity but do not generally lead to improved ammonia utilization by the rumen microorganisms and often in fact reduce such utilization. Urea has also been included in forms physically combined with an energy source e.g. starch or molasses, which assists the microbial uptake of ammonia. The composition of the physical combination may, however, be non-uniform initially or may become non-uniform on storage so that the supply of the energy source does not match that of the ammonia and the risk of toxicity remains.

More recently in the course of academic studies of bacterial metabolism in the rumen, mono-glucosyl urea has been administered to sheep either mixed with the diet or directly into the rumen. This material is not, however, economically practicable as a ruminant feedstuff.

Compounds have now been found which overcome the problems of ammonia toxicity and encourage the incorporation of ammonia into microbial protein by simultaneously providing an energy source for microbial synthesis, which also may be advantageously prepared from waste material.

Accordingly the present invention comprises the use of a compound as a ruminant feedstuff or feedstuff supplement, which compound has the general formula

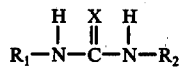

where
$R_1$ = lactosyl
$X$ = O, S or NH
$R_2$ = H, glycosyl or alkyl
A salt of such a compound may be used.

Preferably X is O and the compound of the formula is a derivative of urea. When $R_2$ is glycosyl it may be the residue of a mono- or disaccharide, for instance glucosyl, galactosyl, xylosyl or especially lactosyl. Also when $R_2$ is alkyl having up to 7 carbon atoms it may be substituted or unsubstituted alkyl and is preferably lower alkyl, for instance methyl, ethyl, propyl, or butyl. Preferably, $R_2$ is a hydrogen atom. The compound of the formula may according to an embodiment be in the form of a salt, for instance a commonly occurring salt such as the phosphate or sulphate.

Representative compounds of the invention are:
1-lactosyl urea
1-lactosyl-3-glucosyl urea
1-lactosyl-3-methyl urea
1-lactosyl-3-propyl urea
1-lactosyl-3-ethyl urea
1-lactosyl thiourea
1-lactosyl-3-glycosyl thiourea
1-lactosyl-3-methyl thiourea
1-lactosyl-3-ethyl thiourea
1-lactosyl-3-propyl thiourea
1-lactosyl guanidine
1-lactosyl-3-glycosyl guanidine
1-lactosyl-3-methyl guanidine
1-lactosyl-3-ethyl guanidine
1-lactosyl-3-propyl guanidine The compounds of particular interest are the ureides of lactose e.g. mono lactosyl urea and di-lactosyl urea, wherein X = O and $R_2$ = H or lactosyl.

The feedstuff or feedstuff supplement may comprise one or both of these compounds or other compounds described by the formula or their salts but may also contain other sources of non-protein nitrogen.

The feedstuffs and feedstuff supplements of the present invention may be presented in any of the forms in which non-protein nitrogen is customarily presented. For example, they may be in the form of a composition comprising a ureide of lactose together with a suitable nutritional base e.g. cereals, root crops, forages, silages, roughages or industrial byproducts such as brans, husks or energy-rich pulps or syrups or mixtures of any of these. Advantageously, the nutritional base may be of comparatively low nitrogen content but high energy content for instance maize silage, sugar beet pulp or tapioca. The feedstuff composition may also comprise minerals, vitamins and other dietary additives such as for instance supplementary fats and proteins. The invention includes compositions which contain no nutritional base or nutritional base only as a minor component, and these compositions are usually in the form of feedstuff supplements and comprise other components, such as supplementary dietary additives, in addition to a nitrogenous compound of the present invention.

The levels of non-protein nitrogen present in these compositions may be varied, for instance in accordance with the procedures of ruminant husbandry, taking into account among other factors, the special breed, sex, age and physiological state of the animal and the proportion of the composition in the total diet. For example, the dietary nitrogen requirement for beef cattle corresponding to a protein intake of up to about 12% by weight of the diet, may be replaced in total or in part by non-protein nitrogen. The higher concentration of crude protein in the diet required by high yielding lactating cows may be supplied at least in part by non-protein nitrogen but it is preferable that some dietary true protein should also be supplied. Thus, for example compositions according to the present invention usually contain from about 1% up to about 50% by weight or more of a nitrogenous compound of the present invention, whereby as a preferred embodiment 50% of the diet nitrogen is based on the nitrogenous compound of the invention. The amount of the nitrogenous compounds of the present invention administered to ruminants varies depending on whether other nitrogen sources are present or not but in general if supplied as the only nitrogen source it can be given ad libitum.

The feedstuff compositions may be presented in a wide range of physical forms, for instance in compacted, granulated, powdered, textured, semiliquid or liquid form. The present invention also includes feedstuff supplements, usually in compacted or granulated form which may be put out to be taken ad libitum by pasturing animals, and may also include supplements in liquid or semi-liquid e.g. slurry form, for instance for feeding to cows whilst they are in a milking room. These supplements may comprise supplementary dietary additives with or without a suitable nutritional base. More usually, however, the feedstuff is in the form of a compacted, granulated, powdered or naturally textured feedstuff concentrate which is fed as part of the ration and comprises a suitable nutritional base.

Compounds of lactose described by Formula may be prepared by chemical reaction of urea or an appropriate derivative of urea such as urea monophosphate, thiourea, guanidine, isobutylidene diurea or biuret with lactose. Usually, the reaction is carried out with at least part of the reactants in solution, for instance aqueous solution and the compounds if desired may be recovered in the form of solid products.

The reaction is carried out under acid conditions and the reaction mixture may be warmed. However, highly acidic conditions and excessive temperatures can lead to degradation of the reactants.

For example, a reaction mixture containing urea and lactose which is 0.2 Molar with respect to sulphuric acid and an incubation temperature of 50° C over a period of 7 days has been found to be satisfactory for preparing mono-lactosyl urea.

Advantageously, milk products may be used as a convenient source of lactose and in particular potential waste products of milk, for instance skimmed milk and especially whey which contains a relatively high proportion of lactose. For example, ureides of lactose may be produced by reaction of whey with urea. Preferably, the whey or products prepared from whey and urea are incubated together under acidic conditions and at elevated temperature e.g. at about 50° C.

According to a preferred embodiment of the invention, the reaction is carried out using urea and lactose containing milk-byproducts in the form of unconcentrated whey, concentrated whey, whey permeate, and/or buttermilk-whey.

Unconcentrated whey is the waste product obtained in cheese production, which whey contains about 4,8% lactose, and in total about 8% dry matter.

Concentrated whey is a whey product from which water has been removed by evaporation and contains about 41% lactose and in total about 62% dry matter.

Whey permeate is a product obtained after reverse osmosis of whey and contains about 50% lactose and in total 65% dry matter.

Buttermilk-whey is a residual product obtained after having prepared a buttermilk protein concentrate from buttermilk. Dried buttermilk-whey containing about 6% water contains about 59% lactose.

The pH of the reaction mixture of urea and whey products is kept between 1,5 and 3,5 preferably at pH 2.

The temperature of the reaction mixture is kept above 40° C but not above about 80° C, whereby the preferred temperature is 60°–70° C.

The reaction time is long enough to give at least a 50% yield of the lactosylureide, which time, depending on concentration of the whey used and the relation between the lactose and urea, may be up to 4 days (96 hrs).

Acids used for acidifying the reaction mixture are selected from the group consisting of strong inorganic acids such as hydrochloric acid, sulfuric acid and phosphoric acid.

Thus, according to a further aspect of the present invention a process for the production of a ruminant feedstuff or feedstuff supplement comprises treating whey with urea or an appropriate derivative of urea so as to convert the lactose present in the whey to a compound or compounds described by the formula.

The products produced from such a treatment of whey are also included within the scope of the present invention. Appropriate derivatives of urea are for example urea monophosphate, thiourea, guanidine, isobutylidene diurea or biuret. It is envisaged, however, that urea would usually be used in carrying out this reaction so that the product would consist predominantly of ureides of lactose. The compounds of the Formula may be separated from the impure product, for instance by evaporation and recrystallization, and may subsequently be used for the preparation of feedstuffs and feedstuff supplements according to the present invention. Preferably, however, the product is recovered in impure form, for instance the solution is neutralized if required, and the impure product may be concentrated e.g. by evaporation or reverse osmosis, or recovered in a solid form e.g. by spray or roller drying. Such an impure product typically comprises ureides of lactose e.g. mono-lactosylurea, together with unconverted lactose and urea and minor proportions of soluble milk proteins and other soluble components. The impure product in solid, liquid or slurry form may be used directly as a ruminant feedstuff supplement, or may be combined in a feedstuff composition with other materials such as for instance cereals, pulps, silage, roughage, preferably with additional fats, oils, proteins, vitamins or minerals.

The invention is illustrated by the following examples which describe the preparation of ruminant feedstuffs from whey.

EXAMPLE 1

Urea (96 g) is added to 2 liters of rennet-precipitated whey containing 4.8% by weight of lactose and the mixture acidified by addition of 90 ml of 25% (v/v) sulphuric acid. The reaction mixture is then incubated at 50° C for 7 days after which time at least 70% of the lactose is converted to ureide, as determined chromatographically (mp 232°–234° C). The incubated reaction mixture is then neutralized by addition of sodium hydroxide, and the impure product recovered in solid form by spray-drying. A ruminant feedstuff is then prepared by mixing the impure solid product with a suitable nutritional base such as maize silage or sugar beet pulp. The ratio by weight of nutritional base dry matter to impure product is in the range 1:1 to 60:1.

Alternatively, the impure product in a solid form is used directly as a ruminant feed supplement; or the ureides of lactose are separated and purified by evaporation of the reaction mixture and recrystallization from, for example, water and subsequently used for preparation of feedstuff compositions.

EXAMPLE 2

The same procedure is followed as in Example 1 above with the difference that the reaction mixture is incubated at 70° C for 15 hrs after which time at least 50% of the lactose is converted to lactosyl ureide, as determined chromatographically (mp 233°–234° C).

EXAMPLE 3

Urea (82 g) is added to 200 g of concentrated whey containing 41% by weight of lactose and the mixture is acidified by the addition of 40 ml 33% (v/v) sulphuric acid to pH 2. The reaction mixture is incubated at 70° C for 15 hrs. Conversion of lactose to lactosyl ureide as determined by chromatography is at least 85%.

EXAMPLE 4

The same procedure is followed as in Example 3 but using concentrated whey permeate containing 50.2% by weight of lactose. Conversion of lactose to lactosyl ureide as determined chromatographically is at least 70%.

EXAMPLE 5

The same procedure is followed as in Example 3 with the difference that 45 ml of concentrated phosphoric acid (1.75 S.G) is added to bring the pH of the mixture to 2. Conversion of lactose to lactosyl ureide, as determined chromatographically is at least 74%.

EXAMPLE 6

The same procedure is followed as in Example 4 with the difference that 60 ml of concentrated phosphric acid (1.75 S.G.) is added to bring the pH of the mixture to 2. Conversion of lactose to lactosyl ureide, as determined chromatographically is at least 70%.

EXAMPLE 7

A feed concentrate intended for dairy cows were prepared. Cows producing about 30 kg milk containing about 4% fat are given about 13 kg of the concentrate per day. Such a daily ration contains Lactosyl ureide of Examples 1–6: 0.7 kg
Barley: 6.0 kg
Oats rolled: 5.5 kg
Beet pulp: 0.5 kg
Vitamins and minerals: 0.3 kg.

Such a concentrate contains about 16% crude protein.

If the concentrate is completed with hay, 8 kg per day, a complete feedingstuff for dairy cows is obtained.

EXAMPLE 8

A complete feedingstuff for beef calves having a live weight of about 200 kg and having a weight increase of 1000–1200 g per day contains hay and a concentrate.

The composition of the daily ration of the concentrate (5–6 kg) is as follows:

Lactosyl ureide of Examples 1–6: 0.180 kg
Barley: 2.5 kg
Oats, rolled: 2.5 kg
Beet pulp: 0.6 kg
Vitamins and minerals: 0.150 kg.

which concentrate contains about 14% crude protein. The concentrate is completed with hay, 0.5 kg per animal per day.

EXAMPLE 9

A feed concentrate for beef calves was prepared containing:

1-lactosyl-3-glycosyl urea: 0.250 kg
Barley: 2.5 kg
Oats, rolled: 2.5 kg
Beet pulp: 0.6 kg
Vitamins and minerals: 0.150 kg.

EXAMPLE 10

A feed concentrate for beef calves was prepared containing:

1-lactosyl-3-ethyl urea: 0.195 kg
Barley: 2.5 kg
Oats, rolled: 2.5 kg
Vitamins and minerals: 0.150 kg.

EXAMPLE 11

A feed concentrate for beef calves was prepared containing:

1-lactosyl-3-glycosyl thiourea: 0.260 kg
Barley: 2.5 kg
Oats, rolled: 2.5 kg
Vitamins and minerals: 0.150 kg.

EXAMPLE 12

A feed concentrate for beef calves was prepared containing:

1-lactosyl guanidine: 0.120 kg
Barley: 2.5 kg
Oats, rolled: 2.5 kg
Vitamins and minerals: 0.150 kg.

The biological effect of the lactosyl ureide according to the present invention was determined in vitro and in vivo in accordance with the following.

One sheep received diets of approximately equal parts of barley and straw, cubed, containing 15.7 g N/kg dry matter. Part of the cubes was then replaced with lactosyl ureide to give diets containing 25.4 g N/kg dry matter, of which nitrogen content one half was contributed by the lactosyl ureide.

In vivo: Small samples of rumen digest were removed and acidified at various times after feeding and the ammonia concentrations were measured. Samples were taken feeding the sheep (1) basal feedstuff, (2) feedstuff supplemented with lactosyl ureide, and (3) feedstuff supplemented with equimolecular amounts of lactose and urea.

Ammonia concentrations were measured during prefeeding periods and postfeeding periods as well. The prefeeding period is the first 6 days of feeding a new feedingstuff.

The ammonia concentrations found feeding feedstuffs 2 and 3 above are given in table 1 below.

Table 1

| Time after feeding (hrs) | Conc. of NH₃ (mM)/l of rumen | | | | | Lactose + urea |
|---|---|---|---|---|---|---|
| | Lactosylureide | | | | | |
| | prefeed | postfeed | | | | postfeed |
| | 2nd day | 5th | 19th | 28th | 34th | 33-35th day |
| 0 | 12.5 | 15.8 | 17.5 | 14.4 | 16.6 | 11.4 |
| 0.5 | 14.3 | 16.1 | 16.2 | 13.8 | 15.1 | 30.2 |
| 1 | 15.2 | 15.4 | 18.4 | 14.6 | 14.7 | 42.5 |
| 2 | 19.9 | 15.4 | 18.3 | 17.6 | 15.1 | 57.8 |
| 4 | 20.5 | 16.3 | 23.8 | 18.3 | 18.4 | 31.0 |
| 6 | 19.2 | 18.9 | 37.4 | 48.7 | 29.2 | 23.9 |

As evident therefrom low ammonia concentrations are obtained after 34 days after adaptation using lactosylureide as a nitrogen source compared with the use of urea as a nitrogen source.

In an in vitro test, samples of rumen contents were taken 2 hrs after feeding basal and were incubated anaerobically at 39° C with (1) lactosyl ureide (42.9 mM/l) and (2) lactose (42.9 mM/l) and urea (42.9 mM/l). Ammonia production and urea disappearance were measured.

On the morning of an in vitro test lactosyl ureide was motted from diet containing high N levels.

The urea disappearance was measured during the prefeeding period and the postfeeding period, respectively. The amounts of the urea remaining in the incubated samples are given in table 2 below.

Table 2

| Time after feeding (hrs) | Conc. of urea (mM/l) | | | |
|---|---|---|---|---|
| | Lactosyl ureide | | Lactose + urea | |
| | Pre-feeding 2nd day | post-feeding 18th day | pre-feeding 2nd day | post-feeding 20th day |
| 0 | 40.6 | 47.7 | 42.2 | 43.7 |
| 0.5 | 39.6 | 45.8 | 40.2 | 33.2 |
| 1 | 40.6 | 45.5 | 37.9 | 21.3 |
| 2 | 41.3 | 43.8 | 31.2 | 2.2 |
| 4 | 40.2 | 38.3 | 21.7 | NIL |
| 6 | 43.8 | 34.4 | 0.9 | NIL |

As evident from the table 2 above urea alone disappears very fast from the samples, whereas lactosylureide does not. This indicates that lactosylureide will not provide high NH₃ levels in the rumen.

In Table 2 above the urea disappearance was given. In Table 3 below the NH₃ production in the same test is given.

Table 3

| Time after feeding (hrs) | Conc. of NH₃ (mM/l) | | | |
|---|---|---|---|---|
| | Lactosyl ureide | | Lactose + urea | |
| | prefeeding 2nd day | postfeeding 18th day | prefeeding 2nd day | postfeeding 20th day |
| 0 | NIL | NIL | 0.5 | 0.7 |
| 0.5 | NIL | NIL | 7.9 | 20.5 |
| 1 | NIL | 2.7 | 12.4 | 33.4 |
| 2 | NIL | 4.5 | 21.7 | 68.8 |
| 4 | NIL | 7.5 | 16.5 | 74.6 |
| 6 | 0.2 | 16.3 | 2.4 | 70.1 |

The conclusion drawn from Table 2 above seems to be correct. Urea alone will give too high NH₃ concentrations in the rumen, while lactosylureide will not.

We claim:

1. A ruminant feedstuff composition for increasing beef and milk production containing as a non-protein nitrogen source an effective amount of a compound of the general formula

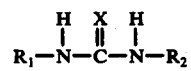

wherein $R_1$ is lactosyl, X is a functional group selected from the group consisting of O, S and =NH, and $R_2$ is a functional group selected from the group consisting of hydrogen, glucosyl and alkyl having 1-4 carbon atoms and a suitable nutritional base.

2. A feedstuff for ruminants according to claim 1, characterized in that it contains lactosyl ureide of said general formula, wherein X is O, and $R_2$ is hydrogen.

3. A method for increasing beef and milk production in ruminants by administering thereto a non-protein nitrogen source which comprises a compound of the general formula

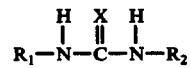

wherein $R_1$ is lactosyl, X is a functional group selected from the group consisting of O, S, and =NH, and $R_2$ is a functional group selected from the group consisting of hydrogen, glucosyl and alkyl having 1 to 4 carbon atoms, which compound is up to about 50% of the daily intake of diet nitrogen.

4. The method according to claim 3 wherein $R_1$ is lactosyl, X is O, and $R_2$ is hydrogen.

5. A method according to claim 4 wherein the compound is administered in an amount of 0.12 to 0.70 kg per day.

6. A method according to claim 3 wherein the compound is administered in an amount of 0.12 to 0.70 kg per day.

* * * * *